(12) United States Patent
Zhang et al.

(10) Patent No.: US 12,105,005 B1
(45) Date of Patent: Oct. 1, 2024

(54) APPARATUS FOR EVALUATING DRIED CRYSTAL ERROR IN $CO_2$ DRYING EXPERIMENT AND USE METHOD THEREOF

(71) Applicant: SOUTHWEST PETROLEUM UNIVERSITY, Chengdu (CN)

(72) Inventors: Ruihan Zhang, Chengdu (CN); Xian Peng, Chengdu (CN); Yongchao Wang, Chengdu (CN); Zihan Zhao, Chengdu (CN); Fei Zhang, Chengdu (CN); Yulong Zhao, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 0 days.

(21) Appl. No.: 18/646,121

(22) Filed: Apr. 25, 2024

(30) Foreign Application Priority Data

Aug. 7, 2023 (CN) .......................... 202310984440.4

(51) Int. Cl.
  *G01N 15/08* (2006.01)
  *G01N 5/04* (2006.01)
  *G01N 33/24* (2006.01)

(52) U.S. Cl.
  CPC ............. *G01N 15/088* (2013.01); *G01N 5/04* (2013.01); *G01N 15/0806* (2013.01); *G01N 33/24* (2013.01)

(58) Field of Classification Search
  CPC .......... G01N 5/04; G01N 15/00; G01N 15/08; G01N 15/0806; G01N 15/088; G01N 33/24

See application file for complete search history.

(56) References Cited

U.S. PATENT DOCUMENTS 9,291,541 B2 * 3/2016 Kim ...................... G01N 15/088

FOREIGN PATENT DOCUMENTS

| CN | 210773106 U |   | 6/2020 |             |
|----|-------------|---|--------|-------------|
| CN | 114136861 A | * | 3/2022 | G01N 15/08  |
| CN | 115753540 A | * | 4/2024 | G01N 15/08  |

OTHER PUBLICATIONS

Machine Translation of CN-114136861-A (Year: 2022).*
Machine Translation of CN-115753540-B (Year: 2024).*

* cited by examiner

*Primary Examiner* — Nguyen Q. Ha
(74) *Attorney, Agent, or Firm* — Birchwood IP

(57) ABSTRACT

An apparatus for evaluating a dried crystal error in a $CO_2$ drying experiment comprises a heating jacket, a visual container, a weighing device, a transparent cover, a control apparatus, a vacuum pump, a damping table and a heating apparatus, and can accurately dry and weigh a rock sample subjected to a carbon dioxide drying effect experiment in the visual container, so that the crystal error caused by evaporation of a solution in the rock sample in the process is calculated. This apparatus provided by the present invention has high precision and simple operation, can well evaluate the crystal error caused by the saline solution retaining in the rock sample when the rock sample is directly dried in the carbon dioxide drying effect experiment, and can correct the results of the carbon dioxide drying effect experiment compared with the prior art, thereby obtaining accurate experiment results.

7 Claims, 2 Drawing Sheets

APPARATUS FOR EVALUATING DRIED CRYSTAL ERROR IN $CO_2$ DRYING EXPERIMENT AND USE METHOD THEREOF

CROSS-REFERENCE TO RELATED APPLICATIONS

This application claims priority to Chinese Patent Application No. 202310984440.4, filed on Aug. 7, 2023, which is hereby incorporated by reference in its entirety.

TECHNICAL FIELD

The present invention relates to the technical field of carbon sequestration experimental equipment, and specifically to an apparatus for evaluating a dried crystal error in a $CO_2$ drying experiment and a use method thereof.

BACKGROUND

Carbon dioxide geological storage technology is one of the effective ways to reduce carbon emissions in the atmosphere. The basic principle of the carbon dioxide geological storage is to transport carbon dioxide captured and then compressed to a supercritical state to deep underground so as to achieve permanent storage, wherein a series of $CO_2$-brine-rock interaction reactions occur during the injection of carbon dioxide, which will affect the storage process of carbon dioxide.

When carbon dioxide is injected into deep saline aquifers with high salt content, water is significantly taken away by diffusion of the carbon dioxide in the saline aquifer due to factors such as pressure gradient differences and concentration differences. That is, water in the saline aquifer is evaporated out by the carbon dioxide, so that the water content in the saline aquifer is significantly reduced, and the salt is crystallized and separated out. This process is called a drying effect. According to the drying effect, the saline aquifers are blocked by the precipitated crystals, which reduces the permeability of the saline aquifers and further hinders the subsequent injection of carbon dioxide. It can be seen that the drying effect is an important factor that cannot be ignored in the $CO_2$-brine-rock interactions, and studying the impact of the drying effect on the carbon dioxide sequestration is a prerequisite for ensuring the effectiveness of carbon dioxide injection. Therefore, the drying effect in the carbon dioxide sequestration process is also studied by academia at home and abroad at present.

Currently, in the conventional carbon dioxide drying experiment, the tests are performed with reference to the experimental process of $CO_2$-brine-rock interactions. That is, rock samples are placed in saline water to examine the diffusion effect of carbon dioxide in the rock samples, and the mass of the salt crystals generated by the carbon dioxide drying effect is calculated after the diffusion effect is completed, wherein compared with the dry rock samples, part of the excess mass is the mass of the salt crystals generated by the drying effect, and the other part is the mass of the saline solution retaining in the rock samples; then, when the mass of the salt crystals generated from the carbon dioxide drying effect is calculated, the wet rock core after the experiment is usually directly dried, then the mass difference between the wet rock core and the dry rock core before the experiment is weighed and measured, the mass difference is used as the mass of the salt crystals generated by the drying effect. It can be seen that, when the wet rock core is dried, the liquid evaporated to dryness is saline water, wherein salt crystals are retained in the rock core, so that the mass of the salt crystals in the saline water is calculated into the mass of the salt crystals generated by the drying effect, resulting in the result of the salt crystal mass of the carbon dioxide drying effect experiment being too large. Since the mass of salt crystals generated by the carbon dioxide drying effect experiment is small, this error will have a significant impact on the results of the carbon dioxide drying effect experiment and cannot be ignored.

SUMMARY

In view of this, the present invention aims to provide an apparatus for evaluating a dried crystal error in a $CO_2$ drying experiment and a use method thereof, which are used to test evaporation error of a saline solution in a carbon dioxide drying effect experiment and can help improve the accuracy of the drying effect experimental test.

To solve at least one of the above technical problems, the present invention provides technical solutions as follows.

Provided is an apparatus for evaluating a dried crystal error in a $CO_2$ drying experiment, which comprises a heating jacket, a visual container, a weighing device, a transparent cover, a control apparatus, a vacuum pump, a damping table and a heating apparatus, wherein the cylindrical transparent cover is detachably arranged on the damping table, the weighing device with a weighing tray at the top is arranged in the transparent cover, the transparent visual container supported by a support is arranged above the weighing device, and the weighing tray extends into the visual container;

a surface of the visual container is provided with the heating jacket that incompletely covers the surface of the visual container, the heating apparatus is arranged on the damping table outside the transparent cover, and the heating jacket is connected to the heating apparatus;

an exhaust pipeline and a vacuum pipeline respectively communicated with the inside and the outside of the transparent cover are arranged on the damping table, and the vacuum pipeline can be connected to an external negative pressure source; and the damping table is further provided with the control apparatus, and the control apparatus is electrically connected to the weighing device and the heating apparatus.

In one embodiment of the present invention, a connection portion between the weighing tray and the weighing device does not contact a wall of the visual container.

Further, the surface of the visual container is provided with an air interchange apparatus, wherein the air interchange apparatus is electrically connected to the control apparatus.

Further, the heating jacket is heated by an electric heating wire and is electrically connected to the heating apparatus.

Further, the vacuum pump is arranged below the damping table, the vacuum pump is connected to the vacuum pipeline, a vacuum valve positioned outside the damping table is arranged on the vacuum pipeline, a buffer tank with a pressure gauge is further arranged on the vacuum pipeline, and the vacuum pump is electrically connected to the control apparatus.

Further, the damping table is provided with a fixed groove that enables an edge of an opened side of the transparent cover to be clamped therein, at least one group of fixed joints are arranged on the edge of one opened side of the transparent cover, and the transparent cover is detachably fixed in the fixed groove by passing through the fixed groove and the fixed joints using fixed screws whose number corresponds to the number of fixed joints.

Further, a camera is arranged outside the transparent cover, wherein the camera can photograph the weighing tray.

In addition, the present invention further provides a use method of the apparatus for evaluating a dried crystal error in a $CO_2$ drying experiment, which comprises the following steps:

step S1: selecting a rock sample for a $CO_2$ drying effect experiment, measuring a pore volume of the rock sample as V, then placing the rock sample into a weighing tray, vacuuming the inside of a transparent cover, and recording mass of the rock sample before reaction as $m_1$ after the rock sample is dried until the mass is stable;

step S2: taking out the rock sample in the step, subjecting the rock sample to the $CO_2$ drying effect experiment, putting the then reacted rock sample into the weighing tray again, vacuuming the inside of the transparent cover, and then weighing wet mass $m_2$ of the then stably reacted rock sample;

step S3: drying the stably reacted rock sample until the mass is stable to obtain dry mass $m_3$ of the stably reacted rock sample;

step S4: calculating a mass difference between $m_3$ and $m_2$ as $m_4$, that is, the mass of evaporated water that is dried after reaction is $m_4$, and further calculating the volume $V_0$ of evaporated water that is dried after reaction, wherein $V_0 = m_4/\rho_0$, $\rho_0$ is a density of water;

step S5: taking a solution with the volume of $V_1$ after reaction in the $CO_2$ drying effect experiment in the step S2, wherein $V_1 = V_0$, and the mass of this solution is $m_5$;

step S6: placing the solution with the volume of $V_1$ after reaction in the step S5 on the weighing tray, and drying the solution under a vacuum condition until the mass of the solution is unchanged to obtain the mass $m_6$ of the salt crystals in this solution;

step S7: completely washing the crystals after drying the solution with the volume of $V_1$ obtained in the step S6 by using alcohol with the volume of $V_0'$ into the alcohol to obtain an alcohol mixed solution, and measuring the volume of the alcohol mixed solution as $V_3$, so as to obtain the volume of the crystals after drying the solution with the volume of $V_1$ as $V_2$, wherein $V_2 = V_3 - V_0'$; and step S8: calculating a porosity error $\varphi^*$ occupied by the crystals after drying the solution with the volume of $V_1$ by using the volume $V_2$ of the crystals after drying the solution with the volume of $V_1$ obtained in the step S7 and the pore volume V of the rock sample for the $CO_2$ drying effect experiment, wherein the porosity error $\varphi^*$ occupied by the crystals after drying the solution with the volume of $V_1$ is the dried crystal error in the $CO_2$ drying experiment, the mass of the dried crystal error in the $CO_2$ drying experiment is $m_6$, and $\varphi^* = V_2/V$.

The present invention has the technical effects as follows.

The present invention provides an apparatus and a method for evaluating crystals generated by evaporating and drying saline water with $CO_2$. This apparatus has the advantages of reliable principle, high precision, complete functions and simple operation, can well evaluate the crystal error caused by the saline solution retaining in the rock sample when the rock sample is directly dried in the carbon dioxide drying effect experiment, and can correct the results of the carbon dioxide drying effect experiment compared with the prior art, thereby obtaining accurate experiment results.

BRIEF DESCRIPTION OF DRAWINGS

To describe the technical solutions in embodiments of the present invention more clearly, the following briefly describes the accompanying drawings used for describing embodiments. It should be understood that the accompanying drawings show only some embodiments of the present invention, and therefore should not be considered as a limitation on the scope. Those of ordinary skill in the art may still derive other related drawings from these accompanying drawings without creative efforts.

DETAILED DESCRIPTION OF EMBODIMENTS

The present invention is further described in detail below with reference to the embodiments and drawings.

To make objectives, technical solutions, and advantages of embodiments of the present invention clearer, the following clearly and completely describes the technical solutions in embodiments of the present invention with reference to the accompanying drawings in embodiments of the present invention. It is clear that the described embodiments are some but not all of embodiments of the present invention. Based on the embodiments of the present invention, all other embodiments obtained by those of ordinary skill in the art without creative effort shall fall within the protection scope of the present invention. Therefore, the following detailed descriptions of embodiments of the present invention provided in the accompanying drawings are not intended to limit the scope of the present invention that claims protection, but merely to represent selected embodiments of the present invention.

Embodiment

Figure 1:
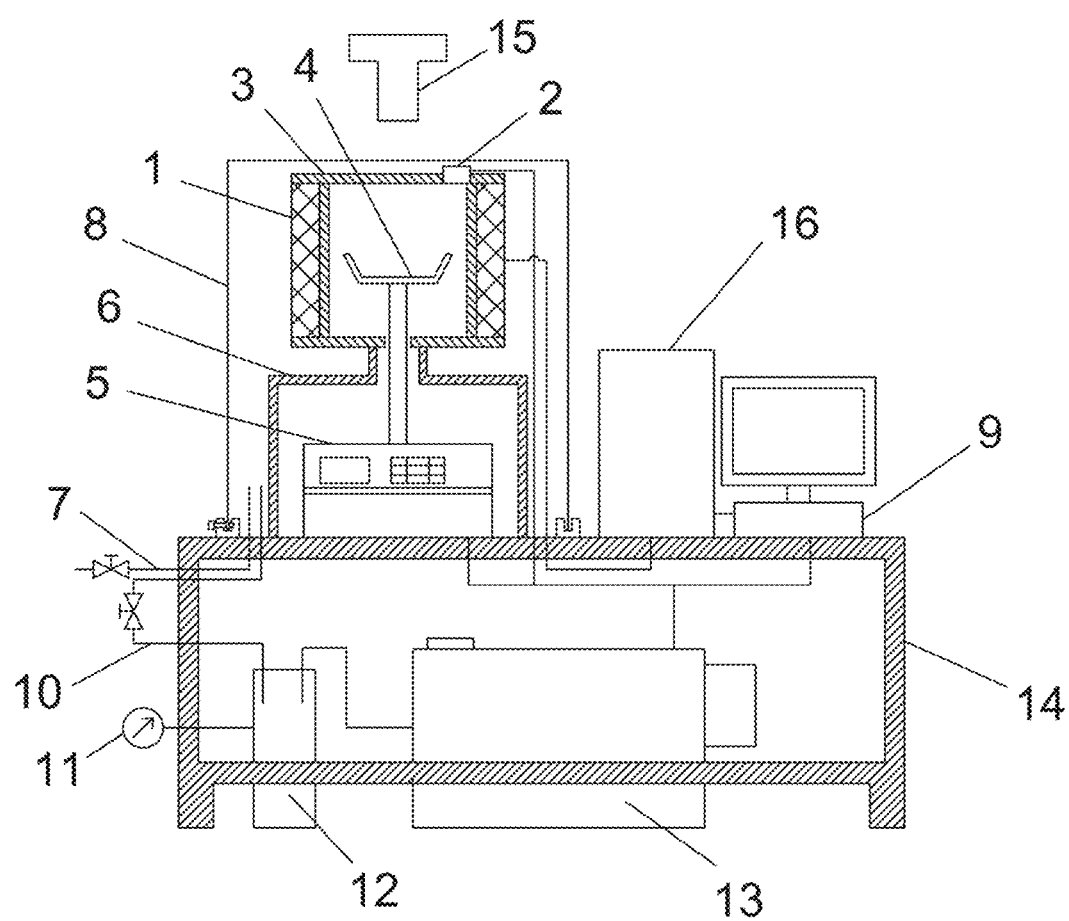
FIG. 1 is a schematic diagram of an overall structure of an apparatus for evaluating a dried crystal error in a $CO_2$ drying experiment according to the present invention.

FIG. 1 shows an apparatus for evaluating a dried crystal error in a $CO_2$ drying experiment. A cylindrical transparent cover 8 is detachably arranged on a damping table 14, wherein the transparent cover has a structure including but not limited to a cylinder, a prism and a rectangular column, and is made of a material including but not limited to glass and transparent polymer. In this embodiment, the cylindrical transparent cover made of high pressure glass is used. A weighing device 5 with a weighing tray 4 at the top is arranged in the transparent cover, which can weigh a rock sample on the weighing tray 4; a transparent visual container 3 supported by a support 6 is arranged above the weighing device 5, and the transparent visual container 3 must be pressure-resistant and light-transmitting, preferably a container consisting of high-pressure glass; the weighing tray 4 extends into the visual container 3, so that the rock sample can be weighed in the visual container 3; and it is clear that the visual container 3 should be provided with at least one surface with a detachable structure to allow a rock sample cup to be placed in the weighing tray 4.

A surface of the visual container 3 is provided with a heating jacket 1 that incompletely covers the surface of the visual container, the purpose of incomplete covering is to leave a visual field, thereby allowing observation of the rock sample inside the visual container 3. A heating apparatus 16 is arranged on the damping table 14 outside the transparent cover 8, and the heating jacket 1 is connected to the heating apparatus 16. The heating jacket 1 is heated by a mode including but not limited to medium heat conduction, electromagnetic induction heating and heating wire heating, and considering the apparatus cost, the heating jacket 1 is heated by the electric heating wire in this embodiment and is electrically connected to the heating apparatus 16.

An exhaust pipeline 7 and a vacuum pipeline 10 respectively communicated with the inside and the outside of the transparent cover 8 are arranged on the damping table 14, the vacuum pipeline 10 can be connected to an external negative pressure source, and the function of the vacuum pipeline 10 is to maintain a certain degree of vacuum inside the transparent cover 8. Since the visual container 3 is not completely sealed, the rock sample in the container can be effectively evaporated under the vacuum condition and the combined action of the heating device; and when the vacuum condition needs to be relieved, the pressure balance can be achieved by opening the exhaust pipeline 7.

The damping table 9 is further provided with a control apparatus 14, the control apparatus 9 is electrically connected to the weighing device 5 and the heating apparatus 16, that is, the control apparatus 9 is used as a workstation to perform unified central control on the electronic devices in the apparatus, and the connection and disposing manners of the control apparatus belong to the prior art and are not described again.

In some embodiments, a connection portion between the weighing tray 4 and the weighing device 5 does not contact a wall of the visual container 3, which avoids the weighing of the weighing tray 4 from being interfered by the inner wall of the visual container 3.

In some embodiments, the surface of the visual container 3 is provided with an air interchange apparatus 2, and the air interchange apparatus 2 is electrically connected to the control apparatus 9, which improves the gas exchange inside the visual container 3, and improves the evaporation efficiency when water in the rock sample is evaporated.

In this embodiment, a vacuum pump 13 is arranged below the damping table 14, the vacuum pump 13 is connected to the vacuum pipeline 10, that is, the apparatus provides a vacuum degree for the integrated device, and a vacuum valve positioned outside the damping table 14 is arranged on the vacuum pipeline 10, so that a user can conveniently operate the on/off of the vacuum pipeline 10. A buffer tank 12 with a pressure gauge 11 is further arranged on the vacuum pipeline 10, and the vacuum pump 13 is electrically connected to the control apparatus 9.

Figure 2:
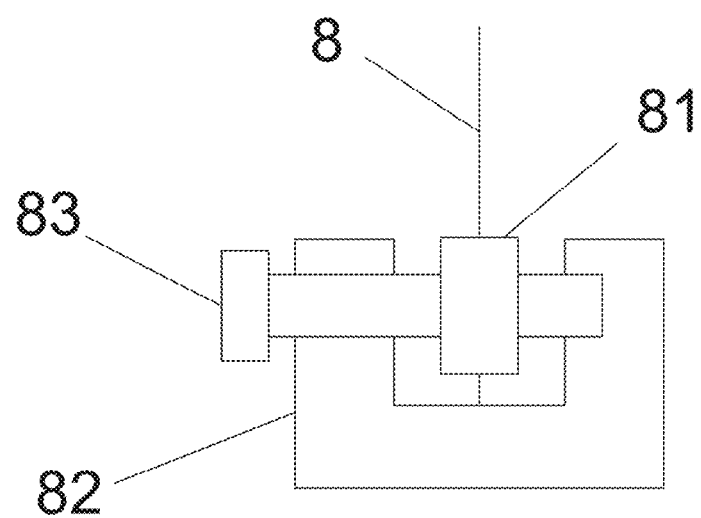
FIG. 2 is a partially enlarged view of a fixed portion of a transparent cover; and in the drawings, 1: heating jacket, 2: air interchange apparatus, 3: visual container, 4: weighing tray, 5: weighing device, 6: support, 7: exhaust pipeline, 8: transparent cover, 9: control apparatus, 10: vacuum pipeline, 11: pressure gauge, 12: buffer tank, 13: vacuum pump, 14: damping table, 15: camera, 16: heating apparatus, 81: fixed joint, 82: fixed groove, and 83: fixed bolt.

The transparent cover 8 is mounted in consideration of sealing performance, stability and detachability, and is thus provided in the manner described in this embodiment. As shown in FIG. 2, the damping table 14 is provided with a fixed groove 82 that enables an edge of an opened side of the transparent cover 8 to be clamped therein, one group of fixed joints 81 are arranged on the edge of one opened side of the transparent cover 8, and the transparent cover 8 is detachably fixed in the fixed groove 82 by passing through the fixed groove 82 and the fixed joints 81 using fixed screws 83 whose number corresponds to the number of fixed joints 81. That is, when the transparent cover 8 is required to be arranged after the rock sample is placed, the transparent cover 8 is placed in the fixed groove 82, so that the through hole of the fixed joint 81 on the transparent cover 8 is aligned with the through hole on the fixed groove 82, and then the fixed screw 83 is screwed into the through holes of the fixed joint and the fixed groove, so that the transparent cover 8 can be fixed.

In some embodiments, a camera 15 is arranged outside the transparent cover 8, wherein the camera 15 can photograph the weighing tray 4, and can record specific changes in the rock core drying process; and the image capture range of the camera 15 should include the portion not completely covered by the heating jacket 1.

It can be seen that the apparatus for evaluating a dried crystal error in a $CO_2$ drying experiment in the present invention can provide a stable and accurate testing environment for drying the rock sample subjected to the carbon dioxide drying experiment, and can be used for accurately determining the actual crystal mass generated by the carbon dioxide drying effect while measuring the crystal error caused by evaporating retained saline water.

The use method of the apparatus for evaluating a dried crystal error in a $CO_2$ drying experiment comprises the following steps:

Step S1: selecting a rock sample for a $CO_2$ drying effect experiment, measuring a pore volume of the rock sample as V, then placing the rock sample into a weighing tray, setting the entire apparatus according to the structure of FIG. 1, vacuuming the inside of a transparent cover, and recording mass of the rock sample before reaction as $m_1$ after the rock sample is dried until the mass is stable;

the basic mass $m_1$ of the dried rock sample is weighed by the above apparatus under a specific condition, and the pore volume V is usually measured by a drainage method using pure water, which is advantageous for removing all the liquid in the rock sample under a high-temperature and negative-pressure condition of the apparatus.

Step S2: taking out the rock sample in the step S1, subjecting the rock sample to the $CO_2$ drying effect experiment, putting the then reacted rock sample into the weighing tray again, vacuuming the inside of the transparent cover, and then weighing wet mass $m_2$ of the then stably reacted rock sample;

after the rock sample is used for reaction, two parts of mass are mainly increased compared with the dried rock sample: one part of mass is the mass of crystalline salt precipitated from the saline water in the dried rock sample after the water is dried and evaporated by the carbon dioxide, the other part of the mass is the mass of retained saline water in the rock sample after reaction; to accurately obtain the mass of the crystalline salt precipitated from the saline water in the dry rock sample, it is necessary to calculate the mass of the retained saline water in the rock sample after reaction, and therefore the wet mass $m_2$ obtained by weighing in this case is the sum of the mass of the dried rock sample and the mass of the two excess parts.

Step S3: drying the stably reacted rock sample until the mass is stable to obtain dry mass $m_3$ of the stably reacted rock sample;

after the step is performed, water in the retained saline water is removed, the retained salt is left in the rock sample, the weight obtained by the direct drying process adopted by the conventional test is the sum of the retained salt and the carbon dioxide dried crystalline salt, that is, the error of the retained salt is introduced and needs to be removed, so that the total mass $m_3$ of the dried rock sample after the reaction is firstly calculated for subsequent calculation.

Step S4: calculating a mass difference between $m_3$ and $m_2$ as $m_4$, that is, the mass of evaporated water that is dried after reaction is $m_4$, and further calculating the volume $V_0$ of evaporated water that is dried after reaction, wherein $V_0 = m_4/\rho_0, \rho_0$ is a density of water;

the mass difference $m_4$ between $m_3$ and $m_2$ is the mass of pure water evaporated out by the apparatus when the reacted rock sample is dried, namely, the solvent for dissolving the retained salt, so that the volume $V_0$ occupied by water with the mass of $m_4$ can be calculated from the density of water.

Step S5: taking a solution with the volume of $V_1$ after reaction in the $CO_2$ drying effect experiment in the step S2, wherein $V_1 = V_0$, and the mass of this solution is $m_5$;

since the common inorganic salts dissolved in water in the formation have almost a negligible impact on the volume of the solution, the reacted saline water with the volume of $V_1$ is taken out, and when $V_1 = V_0$, the taken-out reacted saline water with the volume of $V_1$ may be equivalent to the retained saline water; therefore, the data related to the reacted saline water with the volume of $V_1$ may be equivalent to the data related to the retained saline water.

Step S6: placing the solution with the volume of $V_1$ after reaction in the step S5 on the weighing tray, and drying the solution under a vacuum condition until the mass of the solution is unchanged to obtain the mass $m_6$ of the salt crystals in this solution;

the reacted saline solution with the volume of $V_1$ is placed in a container of known weight instead of the retained water, vacuum heating and drying is performed in the above apparatus, conditions such as temperature and vacuum degree are adjusted according to the experiment requirement, and thereafter the salt crystals with the mass of $m_6$ left in the container of known weight on the weighing tray can be considered to represent the aforementioned retained salt. It can be seen that the mass of the aforementioned retained salt is $m_6$.

Step S7: completely washing the crystals after drying the solution with the volume of $V_1$ obtained in the step S6 by using alcohol with the volume of $V_0'$ into the alcohol to obtain an alcohol mixed solution, and measuring the volume of the alcohol mixed solution as $V_3$, so as to obtain the volume of the crystals after drying the solution with the volume of $V_1$ as $V_2$, wherein $V_2 = V_3 - V_0'$;

since the alcohol does not dissolve inorganic salts in the formation, by testing the volume difference before and after washing the retained salt with the alcohol, it can be calculated that the volume of retained salt, namely the volume of crystals after drying the solution of volume $V_1$, is $V_2$.

Step S8: calculating a porosity error $\varphi^*$ occupied by the crystals after drying the solution with the volume of $V_1$ by using the volume $V_2$ of the crystals after drying the solution with the volume of $V_1$ obtained in the step S7 and the pore volume V of the rock sample for the $CO_2$ drying effect experiment, wherein the porosity error $\varphi^*$ occupied by the crystals after drying the solution with the volume of $V_1$ is the dried crystal error in the $CO_2$ drying experiment, the mass of the dried crystal error in the $CO_2$ drying experiment is $m_6$, and $\varphi^* = V_2/V$.

It can be seen from the above steps that the volume of the retained salt is $V_2$ and the mass of the retained salt is $m_6$, so that the porosity error occupied by the retained salt can be further calculated as $\varphi^* = V_2/V$, and the mass $m_7$ of the carbon dioxide dried crystalline salt can be calculated, wherein $m_7 = m_3 - m_1 - m_6$. This accurately obtains the accurate results of the carbon dioxide drying effect experiment while evaluating the retained salt error, and thus provides a more accurate technical solution compared with the prior art.

In the description of the present invention, it should be noted that directions or positional relationships indicated by terms such as "upper", "lower", "front", "rear", "left", "right", "top", "bottom", "in", "out" are those shown based on the accompanying drawings, are merely intended to facilitate and simplify description rather than indicate or imply that the indicated device or element must have a specific direction and be structured and operated according to the specific direction, and should not be construed as limiting the present invention.

The above descriptions are merely preferred specific embodiments of the present invention, however, the protection scope of the present invention is not limited thereto, and any modifications and substitutions that can be easily conceived by those skilled in the art within the technical scope disclosed by examples of the present invention shall fall within the protection scope of the present invention. Therefore, the protection scope of the present invention shall be subject to the protection scope of the claims.

What is claimed is:

1. A method for evaluating a dried crystal error in a $CO_2$ drying experiment, performing evaluation using an apparatus for evaluating a dried crystal error in a $CO_2$ drying experiment by adopting the following steps, and comprising:

step S1: selecting a rock sample for a $CO_2$ drying effect experiment, measuring a pore volume of the rock sample as V, then placing the rock sample into a weighing tray (4), vacuuming the inside of a transparent cover (8), and recording mass of the rock sample before reaction as $m_1$ after the rock sample is dried until the mass is stable;

step S2: taking out the rock sample in the step S1, subjecting the rock sample to the $CO_2$ drying effect experiment, putting the then reacted rock sample into the weighing tray (4) again, vacuuming the inside of the transparent cover (8), and then weighing wet mass $m_2$ of the then stably reacted rock sample;

step S3: drying the stably reacted rock sample until the mass is stable to obtain dry mass $m_3$ of the stably reacted rock sample;

step S4: calculating a mass difference between $m_3$ and $m_2$ as $m_4$, that is, the mass of evaporated water that is dried after reaction is $m_4$, and further calculating the volume $V_0$ of evaporated water that is dried after reaction, wherein $V_0 = m_4/\rho_0, \rho_0$ is a density of water, step S5: taking a solution with the volume of $V_1$ after reaction in the $CO_2$ drying effect experiment in the step S2, wherein $V_1 = V_0$, and the mass of this solution is $m_5$;

step S6: placing the solution with the volume of $V_1$ after reaction in the step S5 on the weighing tray (4), and drying the solution under a vacuum condition until the mass of the solution is unchanged to obtain the mass $m_6$ of the salt crystals in this solution;

step S7: completely washing the crystals after drying the solution with the volume of $V_1$ obtained in the step S6 by using alcohol with the volume of $V_0'$ into the alcohol to obtain an alcohol mixed solution, and measuring the volume of the alcohol mixed solution as $V_3$, so as to obtain the volume of the crystals after drying the solution with the volume of $V_1$ as $V_2$, wherein $V_2=V_3-V_0'$; and step S8: calculating a porosity error $\varphi^*$ occupied by the crystals after drying the solution with the volume of $V_1$ by using the volume $V_2$ of the crystals after drying the solution with the volume of $V_1$ obtained in the step S7 and the pore volume V of the rock sample for the $CO_2$ drying effect experiment, wherein the porosity error $\varphi^*$ occupied by the crystals after drying the solution with the volume of $V_1$ is the dried crystal error in the $CO_2$ drying experiment, the mass of the dried crystal error in the $CO_2$ drying experiment is $m_6$, and $\varphi^*=V_2/V$;

wherein the apparatus for evaluating a dried crystal error in a $CO_2$ drying experiment comprises a heating jacket (1), a visual container (3), a weighing device (5), the transparent cover (8), a control apparatus (9), a vacuum pump (13), a damping table (14) and a heating apparatus (16), wherein the cylindrical transparent cover (8) is detachably arranged on the damping table (14), the weighing device (5) with the weighing tray (4) at the top is arranged in the transparent cover (8), the transparent visual container (3) supported by a support (6) is arranged above the weighing device (5), and the weighing tray (4) extends into the visual container (3);

a surface of the visual container (3) is provided with the heating jacket (1) that incompletely covers the surface of the visual container, the heating apparatus (16) is arranged on the damping table (14) outside the transparent cover (8), and the heating jacket (1) is connected to the heating apparatus (16);

an exhaust pipeline (7) and a vacuum pipeline (10) respectively communicated with the inside and the outside of the transparent cover (8) are arranged on the damping table (14), and the vacuum pipeline (10) can be connected to an external negative pressure source; and the damping table (14) is further provided with the control apparatus (9), and the control apparatus (9) is electrically connected to the weighing device (5) and the heating apparatus (16).

2. The method for evaluating a dried crystal error in a $CO_2$ drying experiment according to claim 1, wherein a connection portion between the weighing tray (4) and the weighing device (5) does not contact a wall of the visual container (3).

3. The method for evaluating a dried crystal error in a $CO_2$ drying experiment according to claim 2, wherein the surface of the visual container (3) is provided with an air interchange apparatus (2), and the air interchange apparatus (2) is electrically connected to the control apparatus (9).

4. The method for evaluating a dried crystal error in a $CO_2$ drying experiment according to claim 3, wherein the heating jacket (1) is heated by an electric heating wire and is electrically connected to the heating apparatus (16).

5. The method for evaluating a dried crystal error in a $CO_2$ drying experiment according to claim 4, wherein the vacuum pump (13) is arranged below the damping table (14), the vacuum pump (13) is connected to the vacuum pipeline (10), a vacuum valve positioned outside the damping table (14) is arranged on the vacuum pipeline (10), a buffer tank (12) with a pressure gauge (11) is further arranged on the vacuum pipeline (10), and the vacuum pump (13) is electrically connected to the control apparatus (9).

6. The method for evaluating a dried crystal error in a $CO_2$ drying experiment according to claim 5, wherein the damping table (14) is provided with a fixed groove (82) that enables an edge of an opened side of the transparent cover (8) to be clamped therein, at least one group of fixed joints (81) are arranged on the edge of one opened side of the transparent cover (8), and the transparent cover (8) is detachably fixed in the fixed groove (82) by passing through the fixed groove (82) and the fixed joints (81) using fixed screws (83) whose number corresponds to the number of fixed joints (81).

7. The method for evaluating a dried crystal error in a $CO_2$ drying experiment according to claim 6, wherein a camera (15) is arranged outside the transparent cover (8), and the camera (15) can photograph the weighing tray (4).

* * * * *